(12) United States Patent
Shen et al.

(10) Patent No.: US 8,906,742 B2
(45) Date of Patent: Dec. 9, 2014

(54) TWO-BEAM LASER ANNEALING WITH IMPROVED TEMPERATURE PERFORMANCE

(71) Applicant: Ultratech, San Jose, CA (US)

(72) Inventors: Xiaohua Shen, Fremont, CA (US); Yun Wang, Saratoga, CA (US); Xiaoru Wang, Fremont, CA (US)

(73) Assignee: Ultratech, Inc., San Jose, CA (US)

( * ) Notice: Subject to any disclaimer, the term of this patent is extended or adjusted under 35 U.S.C. 154(b) by 0 days.

(21) Appl. No.: 14/013,175

(22) Filed: Aug. 29, 2013

(65) Prior Publication Data
US 2014/0004627 A1 Jan. 2, 2014

Related U.S. Application Data

(62) Division of application No. 13/359,936, filed on Jan. 27, 2012, now Pat. No. 8,546,805.

(51) Int. Cl.
| | | |
|---|---|---|
| H01L 21/44 | (2006.01) | |
| H01L 21/48 | (2006.01) | |
| H01L 21/50 | (2006.01) | |
| H01L 21/263 | (2006.01) | |
| H01L 21/268 | (2006.01) | |
| H01L 21/324 | (2006.01) | |
| G01N 21/55 | (2014.01) | |
| H01L 21/66 | (2006.01) | |
| B23K 26/06 | (2014.01) | |
| B23K 26/073 | (2006.01) | |
| B23K 26/08 | (2014.01) | |

(52) U.S. Cl.
CPC .......... *H01L 21/2636* (2013.01); *H01L 21/268* (2013.01); *H01L 21/324* (2013.01); *G01N 21/55* (2013.01); *H01L 22/12* (2013.01); *H01L 22/20* (2013.01); *B23K 26/0608* (2013.01); *B23K 26/0732* (2013.01); *B23K 26/08* (2013.01); *B23K 2201/40* (2013.01)
USPC ............. 438/106; 438/308; 438/14; 438/795; 257/48; 257/57; 257/E21.134; 257/E21.183; 257/E21.187; 257/E21.189; 257/E21.324; 25/E21.333; 25/E21.347; 25/E21.497; 25/E21.499; 25/E21.517

(58) Field of Classification Search
USPC .................. 438/106, 308, 14, 486, 487, 795; 257/57, 48, E21.134, E21.183, 257/E21.187, E21.189, E21.324, E21.333, 257/E21.347, E21.497, E21.499, E21.517
See application file for complete search history.

(56) References Cited

U.S. PATENT DOCUMENTS

| | | | | |
|---|---|---|---|---|
| 7,842,254 | B2 * | 11/2010 | Singh et al. | 422/621 |
| 8,546,805 | B2 * | 10/2013 | Shen et al. | 257/57 |
| 2004/0198028 | A1 | 10/2004 | Tanaka et al. | |
| 2006/0234458 | A1 | 10/2006 | Jennings et al. | |
| 2007/0072400 | A1 | 3/2007 | Bakeman | |

OTHER PUBLICATIONS

Search Report from Austrian Patent Office for counterpart Singapore Patent Application No. 201300183-9; Search report dated Aug. 27, 2013.

* cited by examiner

*Primary Examiner* — David Nhu
(74) *Attorney, Agent, or Firm* — Opticus IP Law PLLC

(57) ABSTRACT

Systems and methods are disclosed for performing laser annealing in a manner that reduces or minimizes wafer surface temperature variations during the laser annealing process. The systems and methods include annealing the wafer surface with first and second laser beams that represent preheat and anneal laser beams having respective first and second intensities. The preheat laser beam brings the wafer surface temperate close to the annealing temperature and the anneal laser beam brings the wafer surface temperature up to the annealing temperature. The anneal laser beam can have a different wavelength, or the same wavelength but different orientation relative to the wafer surface. Reflectivity maps of the wafer surface at the preheat and anneal wavelengths are measured and used to select the first and second intensities that ensure good anneal temperature uniformity as a function of wafer position. The first and second intensities can also be selected to minimize edge damage or slip generation.

17 Claims, 9 Drawing Sheets

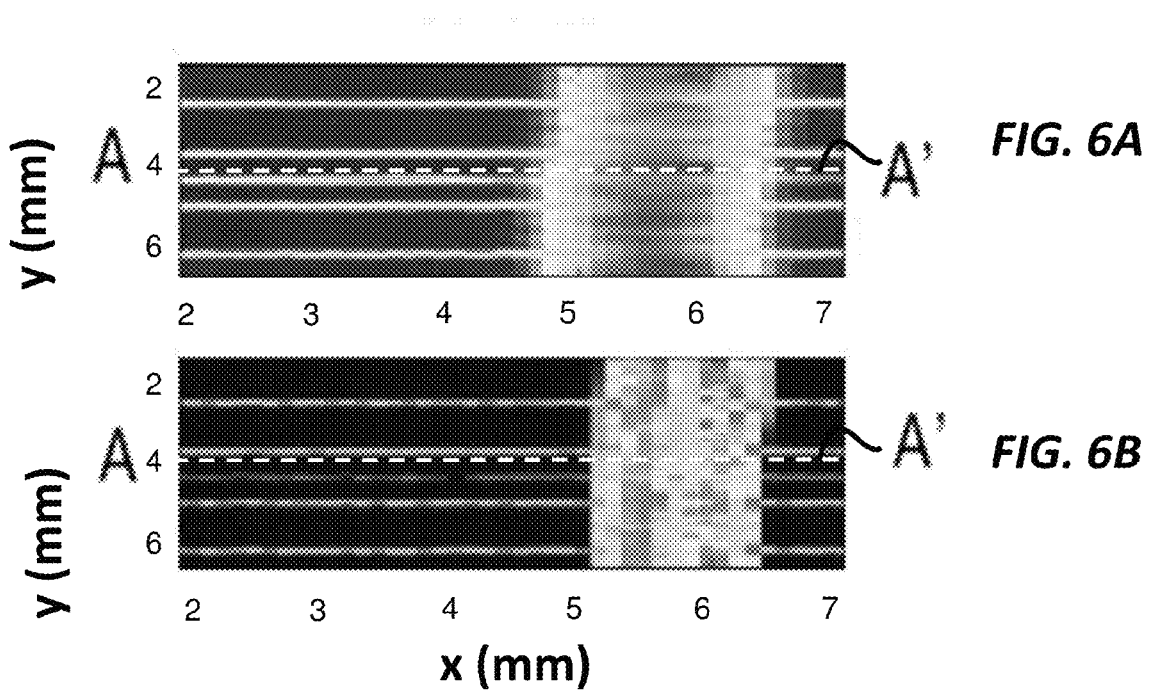
FIG. 6A
FIG. 6B
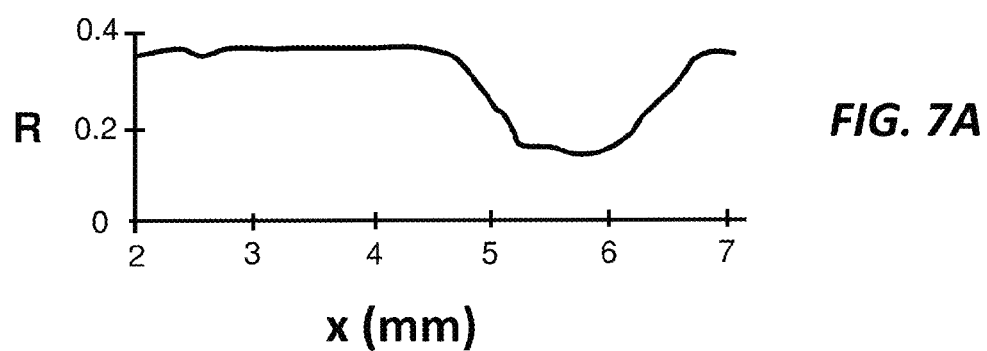
FIG. 7A
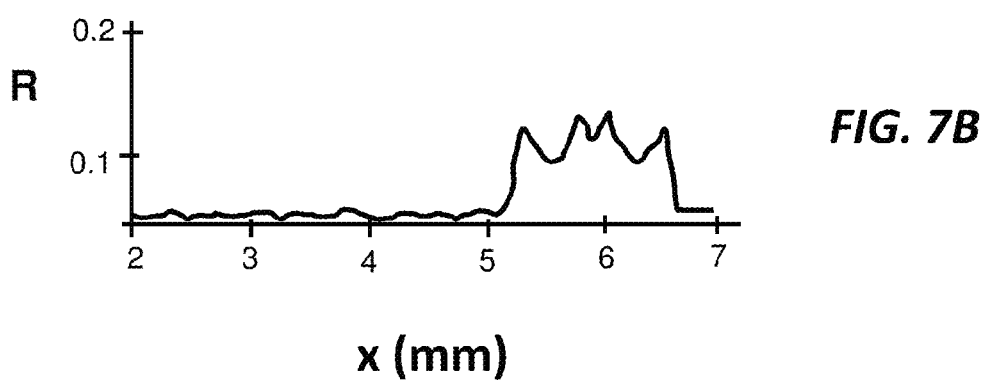
FIG. 7B

TWO-BEAM LASER ANNEALING WITH IMPROVED TEMPERATURE PERFORMANCE

CROSS-REFERENCE TO RELATED APPLICATIONS

This Application is a divisional application of and claims priority from U.S. patent application Ser. No. 13/359,936, filed on Jan. 27, 2012, which has issued as U.S. Pat. No. 8,546,805, and which is incorporated by reference herein.

FIELD

The present disclosure relates generally to annealing as used in semiconductor manufacturing to fabricate integrated circuits, and in particular relates to laser annealing of semiconductor wafers using two laser beams having different wavelengths to improve the temperature performance of the annealing process.

BACKGROUND ART

Millisecond laser annealing, such as laser spike annealing (LSA), has been widely adopted in advanced semiconductor device fabrication because it offers an ultra-low thermal budget, high dopant activation and super-abrupt junctions. A key challenge to implementing this type of annealing on patterned wafers is the potential large within-chip temperature non-uniformities that can arise from spatial variations in the optical and thermal properties of the wafer surface caused by the features of the IC chip. These adverse effects are referred to in the art as "pattern density effects" or just "pattern effects."

In one example of LSA, an infrared laser directs a single annealing laser beam to the wafer surface at or near the Brewster angle of incidence and with a P-polarization to minimize reflections and thus any within-chip temperature non-uniformities due to pattern density effects. The infrared wavelength reduces optical interference effects from the patterns because of its relatively long wavelength (e.g., 10.6 microns) compared to the film thickness (e.g., on the order of 1 micron or less). The Brewster angle of incidence is known to be the angle of maximum absorption for a surface and acts to minimize difference in light absorption due to the IC chip features, including the various thin film stacks used in IC chip fabrication.

This single-beam approach works very well for many IC chip features and circuit layouts. However, for certain IC chip features and for layouts involving large features, temperature overshoots have been observed due to optical diffraction at the boundary between two adjacent regions that have different optical properties. This reduces the maximum annealing temperature that can be used to activate the dopants in the adjacent regions.

FIG. 1 is a close-up cross-sectional view of a section of a prior art silicon wafer 10 having a body 9 and a surface 12. The wafer 10 of FIG. 1 includes a feature in the form of an oxide region (e.g., an oxide isolation pad) 16 formed in wafer body 9 adjacent wafer surface 12. The oxide region feature 16 defines an oxide-silicon interface 17 within wafer body 9 and constitutes an example wafer structure or feature. FIG. 2 is a plot of normalized intensity vs. distance x (μm) from interface 17. The plot shows the simulated optical intensity distribution in the section of wafer 10 shown in FIG. 1 during single-beam laser annealing as performed according to the prior art. The simulation was performed using a P-polarized $CO_2$ laser beam LB (see FIG. 1) at a wavelength of 10.6 μm and incident upon wafer surface 12 at an angle of incidence θ near the Brewster angle $\theta_B$ for a silicon substrate (i.e., $\theta \approx \theta_B \approx 72°$). The intensity plot of FIG. 2 shows a relatively strong intensity oscillation in wafer body 9 adjacent interface 17. The periodicity of the oscillation depends on the angle of incidence θ of laser beam LB, and is typically a fraction of the wavelength.

The corresponding temperature distribution in the wafer section is smoother than the intensity distribution due to thermal diffusion, with a typical heat diffusion length for millisecond laser annealing being about 100 μm. However, the temperature at interface 17 is still higher than that of the rest of wafer body 9. This temperature variation is referred to as edge temperature overshoot $\Delta T_{edge}$. This temperature overshoot can lead to edge damage near features formed in wafer 10.

SUMMARY

Aspects of the disclosure include systems and methods for performing laser annealing using two laser beams having different wavelengths, while other aspects of the disclosure use two laser beams having the same wavelength but a different configuration, i.e., at least one of a different polarization, a different angle of incidence and a different plane of incidence. The systems and methods improve the temperature uniformity of the wafer surface during the annealing process. For wafers whose annealing temperature is limited by slip generation, the two-beam annealing systems and methods disclosed herein can be used to increase the maximum annealing temperature that can be applied without causing slip.

Measurements performed on semiconductor wafers indicate that the wafer surface reflectivity can vary significantly as a function of wafer surface position as well as of the laser wavelength, polarization, angle of incidence and the incident plane orientation with respect to the features formed on the wafer surface. The two-wavelength annealing approach described herein can reduce and in some cases substantially compensate for reflectivity variations and thereby improve the anneal temperature uniformity even within individual IC chips.

The use of the systems and methods disclosed herein to improve within-chip temperature uniformity (as compared to conventional single-beam annealing approaches) is particularly useful when annealing wafers having devices formed with materials that cause high surface reflectivity at infrared wavelengths. In this case, the ratio of the intensities of the two laser beams can be optimized or can be varied as a function of wafer surface position to achieve a minimum optical absorption contrast, which in turn leads to improved anneal temperature uniformity.

Accordingly, aspects of the disclosure include systems and methods for performing laser annealing of a semiconductor wafer during integrated circuit (IC) chip manufacturing by combining first and second laser beams. The first laser beam is an infrared P-polarized laser beam incident upon the wafer surface at or near the Brewster angle $\theta_B$ of silicon (i.e., about 75 degrees). The first laser beam is a preheat laser beam that heats the wafer surface to an intermediate temperature that is typically within several hundred degrees centigrade or so of the target peak annealing temperature. The second laser beam can be an infrared, a visible, or a UV laser beam. The second laser beam can have the same infrared wavelength as the first laser beam but then must have a different configuration, i.e., at least one of a different polarization, a different angle of incidence and a different plane of incidence. If the second laser beam has a substantially different wavelength from the first laser beam, then it can have substantially the same beam configuration, i.e., lie in the same incident plane and have the same or close to the same incident angle. Of course, the second laser beam can also have a different wavelength and a different configuration from the first laser beam. The second laser beam can be incident upon the wafer surface anywhere from near-normal incidence to a large angle, e.g., the Brewster's angle $\theta_B$ or beyond. The second laser beam is used to heat the wafer surface to an annealing temperature $T_A$, which in an example is just below the wafer melt temperature. In an example, the second laser beam increases the wafer surface temperature by between 200° C. and 800° C. The first and second laser beams form respective first and second line images on the wafer surface. In an example, the first line image encompasses the second line image, i.e., the second line image falls within the first line image. The first and second line images move across the wafer surface in synchrony. Such movement can be accomplished by moving the wafer, by moving the line images, or by a combination of these two movements.

A second aspect of the disclosure is a method of combining two laser beams to improve the annealing temperature uniformity as described above, and further includes performing the annealing based on reflectivity maps at the preheat and anneal wavelengths and for the portion of the wafer surface to be annealed. Thus, the method includes measuring the reflectivity of at least a portion of the wafer surface for the respective preheat and anneal wavelengths $\lambda_1$ and $\lambda_2$ to obtain first and second reflectivity maps. Then, using the first and second reflectivity maps, the method also includes annealing the wafer surface using first and second laser beam intensities $I_1$ and $I_2$ that reduce the temperature variation in the wafer surface as compared to using a single laser beam for annealing. In an example, at least one of first laser beam intensity $I_1$ and second laser beam intensity $I_2$ is varied as a function of the wafer surface position in a manner that reduces or minimizes variations in the wafer surface temperature as compared to annealing the wafer surface with a single anneal laser beam.

The third aspect of the disclosure is a method of defining intensities $I_1$ and $I_2$ of the two laser beams to reduce or mitigate edge damage near large features or slip generations formed in the wafer surface. In an example, the intensity $I_2$ of the second laser beam is selected by performing experiments on test wafers over a range of second intensities and establishing the second intensity associated with a reduced or minimum amount of edge damage or a slip generation threshold temperature. The amount of edge damage or slip generation of the test wafers is determined by inspection, e.g., by optical microscope inspection.

Additional features and advantages of the disclosure are set forth in the detailed description that follows, and in part will be readily apparent to those skilled in the art from that description or recognized by practicing the embodiments as described herein, including the detailed description which follows, the claims, as well as the appended drawings. The claims constitute part of this specification, and are hereby incorporated into the detailed description by reference.

It is to be understood that both the foregoing general description and the following detailed description presented below are intended to provide an overview or framework for understanding the nature and character of the disclosure as it is claimed. The accompanying drawings are included to provide a further understanding of the disclosure, and are incorporated into and constitute a part of this specification. The drawings illustrate various embodiments of the disclosure, and together with the description serve to explain the principles and operations of the disclosure.

The claims set forth below constitute part of this specification and in particular are incorporated into and constitute part the Detailed Description set forth below.

BRIEF DESCRIPTION OF THE DRAWINGS

FIG. 6A and FIG. 6B are two-dimensional (x,y) gray-scale reflectivity maps of a portion of an example wafer surface as measured at the preheat wavelength $\lambda_1$ (FIG. 6A) and at the anneal wavelength $\lambda_2$ (FIG. 6B);

FIG. 7A and FIG. 7B are plots of reflectivity R vs. position x (mm) (i.e., one-dimensional reflectivity maps) based on the reflectivity maps FIG. 6A and FIG. 6B respectively, as taken along the white dashed lines A-A';

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure. In some of the Figures, Cartesian coordinates are provided for the sake of reference and are not intended as providing limitations on specific directions and orientations of the systems and methods described herein. The claims as set forth below are incorporated into and constitute part of this detailed description.

In the discussion below, the term "semiconductor substrate" and "wafer" are synonymous and used interchangeably. Likewise, the terms "semiconductor wafer surface" and "wafer surface" are synonymous and used interchangeably, with "wafer surface" being shorthand for "semiconductor wafer surface." The term "wafer" is shorthand for "semiconductor wafer" such as is used in the fabrication of integrated circuit devices. An exemplary wafer is a silicon wafer.

Figure 1:
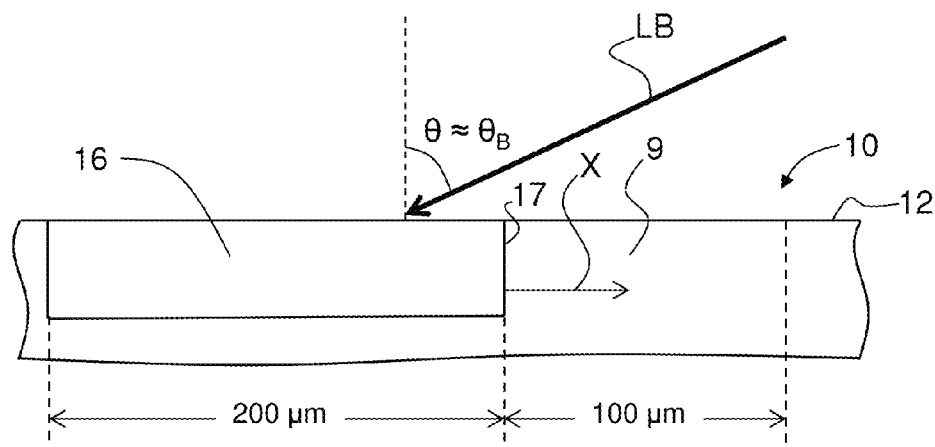
FIG. 1 is a close-up cross-sectional view of a section of a prior art silicon wafer that includes an oxide region formed in the wafer body and adjacent wafer surface, and shows a scanned anneal laser beam passing over the wafer surface.
Figure 2:
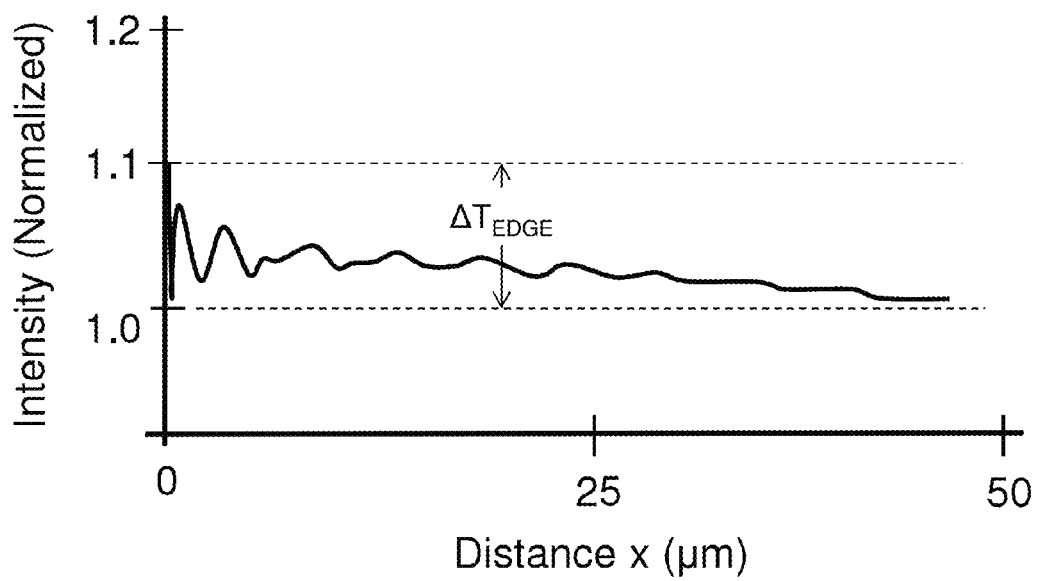
FIG. 2 is a plot of normalized intensity vs. the distance x (μm) into the wafer body from the oxide-silicon interface of FIG. 1, with the plot showing the simulated laser optical intensity distribution in the silicon section of the wafer body during laser annealing as performed according to the prior art, and also showing the edge overshoot temperature $\Delta T_{EDGE}$ that can cause edge damage to the wafer at the edge of the oxide region.
Figure 3:
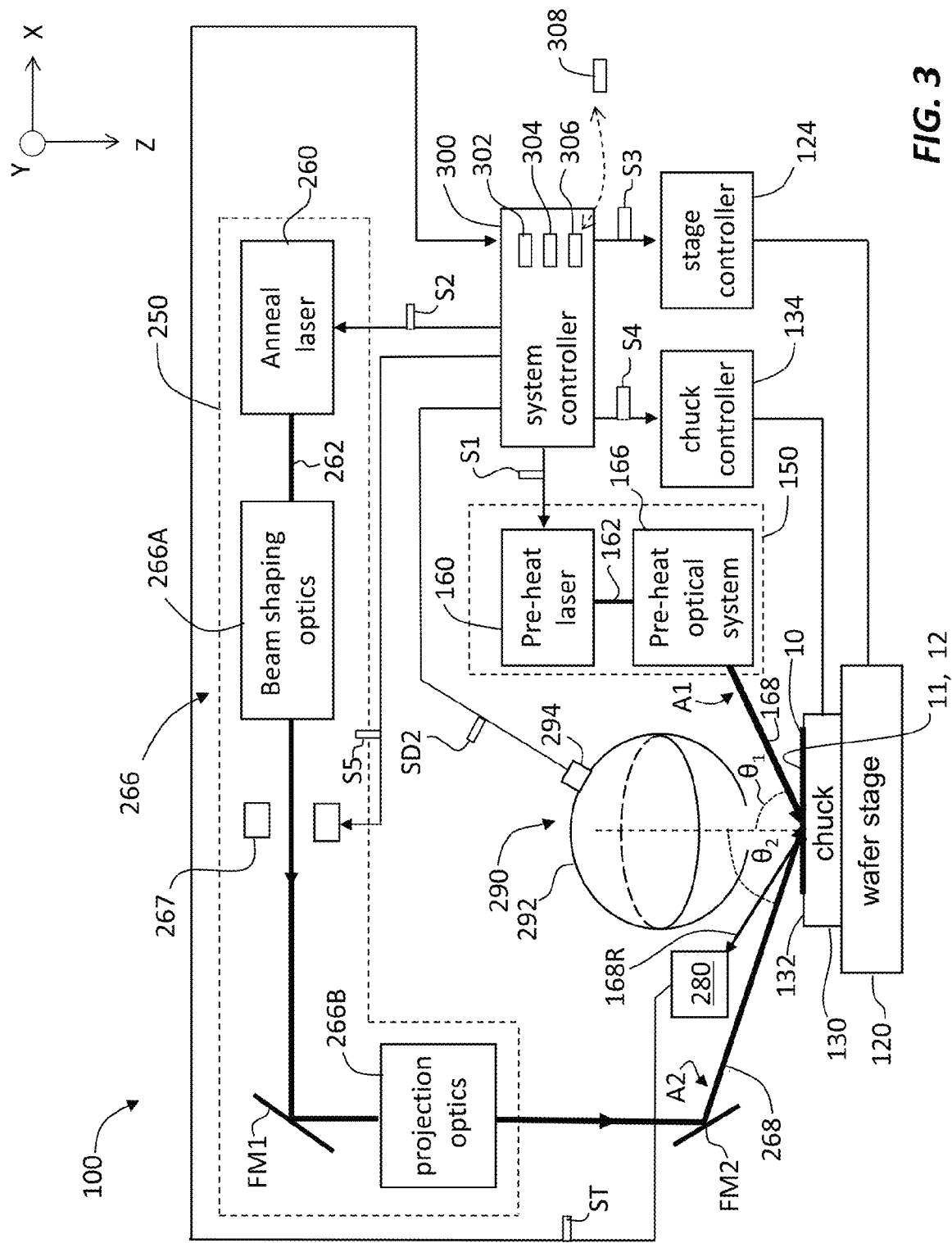
FIG. 3 is a schematic diagram of an example embodiment of a laser annealing system according to the disclosure.
Figure 4A:
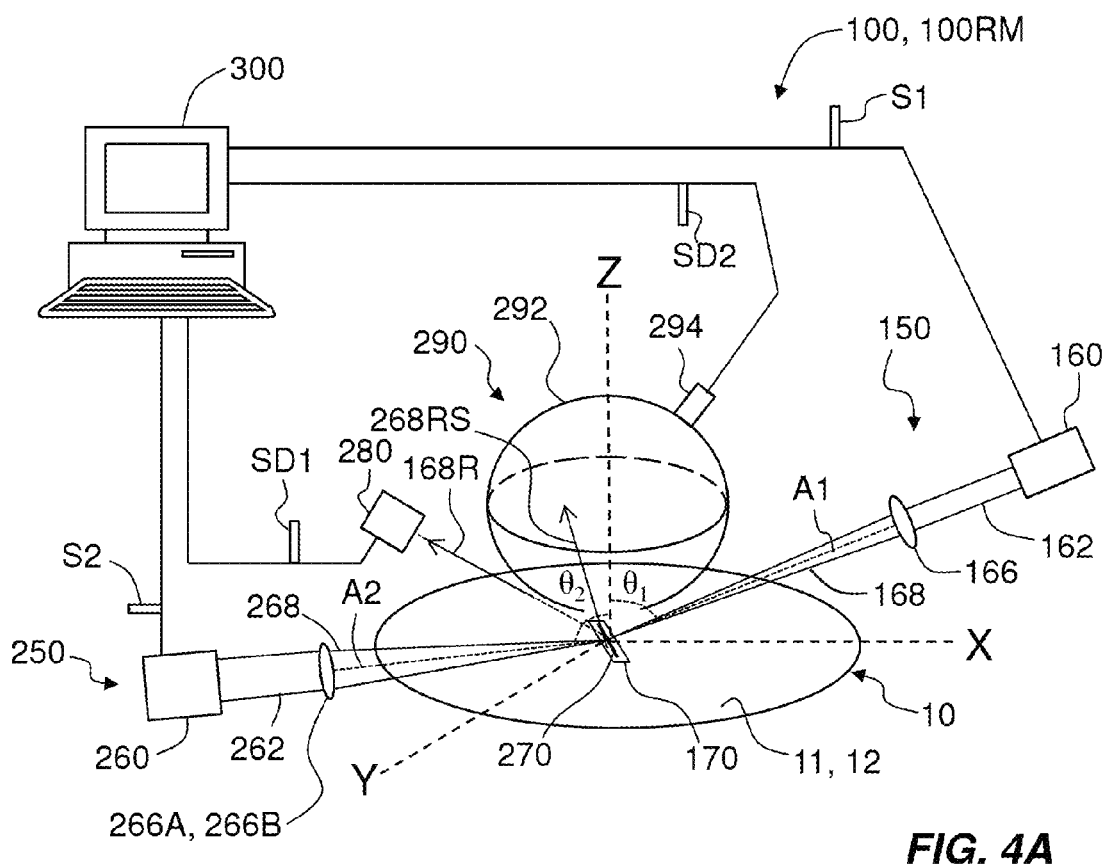
FIG. 4A is a schematic elevated view of an example laser annealing system or an example wafer reflectivity measurement system, illustrating different configurations for the preheat laser beam (first light beam-source system) and the anneal laser beam (second light beam-source system)

FIG. 3 is a schematic diagram of an example embodiment of a laser annealing system ("system") 100 according to the disclosure. FIG. 4A is a schematic elevated view of example system 100. The system 100 of FIG. 4A can also be a wafer reflectivity measurement system 100RM, as discussed below.

With reference to FIG. 3, system 100 includes a wafer stage 120 that operably supports a chuck 130 having an upper surface 132. The wafer stage 120 is configured to move in the X-Y plane and optionally in the Z-direction. The chuck upper surface 132 is configured to operably support a wafer 10 having a body 9 and a planar surface 11 that operably supports a patterned wafer surface 12. The wafer surface 12 can have any pattern that is associated with the various stages of fabricating IC chips and IC chip features (see e.g., the example wafer features 16 in FIG. 5E, introduced and discussed below).

In an example, chuck 130 is heated so that wafer 10 can be preheated. The wafer stage 120 is operably connected to a wafer stage controller 124, and chuck 130 is operably connected to a chuck controller 134.

With reference to FIG. 3 and FIG. 4A, system 100 also includes a first light beam-source system 150 that in an example is configured to generate a first light beam 168 having a first wavelength $\lambda_1$. In an example, first light beam 168 is a laser beam having an intensity $I_1$ and is used to preheat wafer surface 12 by raising wafer surface temperature $T_S$ to be in the range of from about 500° C. to about 1,100° C., which is below the wafer anneal temperature $T_A$, in an example, about 1,300° C.

In another example, system 100 constitutes or is otherwise used as a reflectivity measurement system 100RM, and first light beam 168 is narrow-band light centered at the IR processing wavelength for annealing and is used to measure a first reflectivity $R_1(x,y)$ of wafer surface 12 at first wavelength $\lambda_1$, as described below. As the discussion below is initially directed to laser annealing and later to reflectivity measurement, for convenience first light beam-source system 150 is hereafter referred to as the preheat laser system 150 and first light beam 168 is also referred to as the preheat laser beam 168.

An example preheat laser system 150 includes a preheat laser 160 and a preheat optical system 166 that defines a first optical axis A1. The preheat laser 160 can include a diode laser or a $CO_2$ laser, such as a continuous-wave (CW), P-polarized 10.6 micron $CO_2$ laser. The axis A1 can be oriented so that preheat laser beam 168 is incident upon wafer surface 12 at an incidence angle $\theta_1$ that is in the range of from near normal (i.e., near 0 degrees) to a large oblique incident angle, such as the Brewster angle for silicon, or larger. In an example embodiment, first optical axis A1 has an angle $\theta_1$ that is substantially equal to the Brewster's angle for silicon, so that aforementioned pattern density effects from non-uniform optical absorption are reduced or minimized.

The preheat optical system 166 is configured to receive an initial preheat laser beam 162 and form therefrom preheat laser beam 168. The preheat laser beam 168 travels generally along first (preheat) optical axis A1 and forms a first (preheat) line image 170 at wafer surface 12.

Figure 5A:
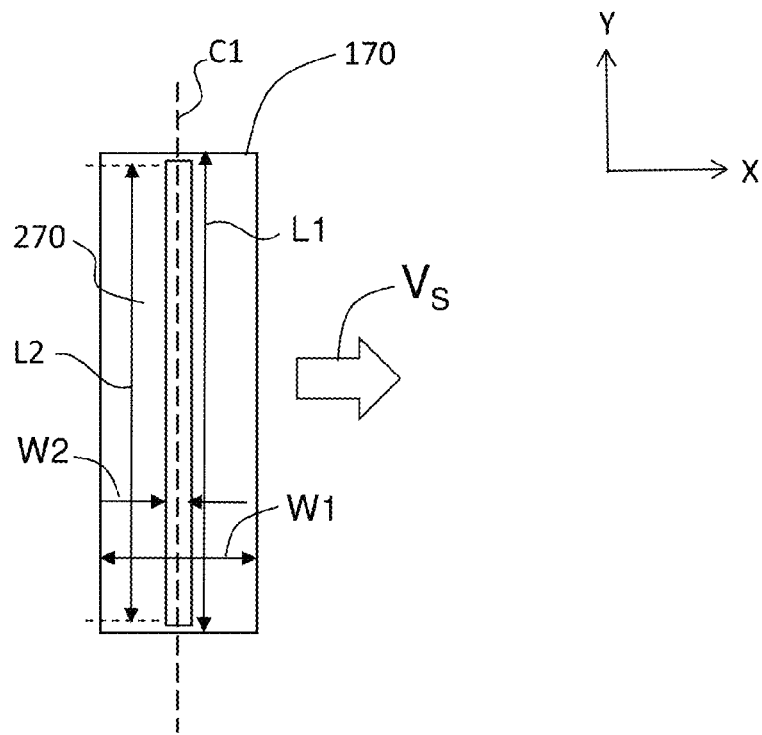
FIG. 5A is a plan schematic view of example idealized preheat and anneal line images as formed on the wafer surface.
Figure 5B:
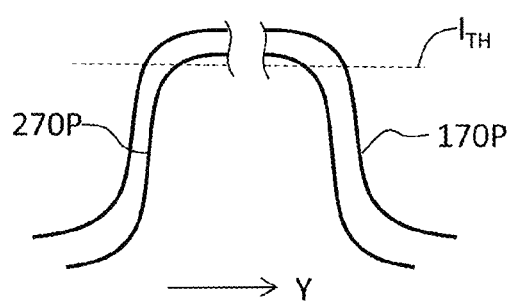
FIG. 5B and FIG. 5C are schematic plots of example intensity profiles for the preheat and anneal line images as taken in the Y-direction (FIG. 5B) and X-direction (FIG. 5C)
Figure 5C:
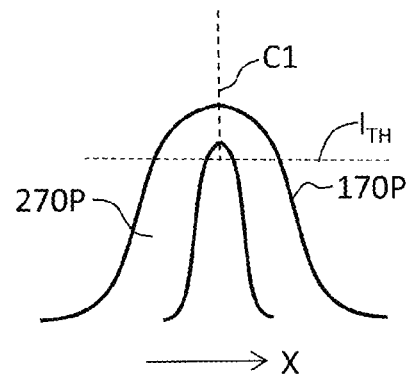

FIG. 5A is a plan schematic view of an example idealized preheat line image 170 as formed on wafer surface 12. FIG. 5B and FIG. 5C are schematic plots of an example intensity profile 170P for preheat line image 170 as taken in the Y-direction (FIG. 5B) and X-direction (FIG. 5C). The intensity profile 170P corresponds to that of preheat laser beam 168 at wafer surface 12 and defines preheat line image 170, e.g., by virtue of the intensity being above a certain threshold intensity $I_{TH}$. The preheat line image 170 is shown as having a centerline or axis C1 in the long (i.e., Y) direction, which is perpendicular to the scan (i.e., X) direction. The preheat line image 170 is scanned in the X-direction at a velocity $V_S$ as indicated by the large arrow in FIG. 5A.

A typical preheat laser beam 168 has a Gaussian intensity profile in the scanning direction and a relatively flat top profile in the long (cross-scanning) direction. An example beam width W1 (defined at full width half maximum (FWHM) of the Gaussian profile) for preheat laser beam 168 (and thus for preheat line image 170) is in the range of from about 0.05 mm to about 2 mm. An example beam length L1 for preheat laser beam 168 (and thus for preheat line image 170) is typically in the range of from about 5 mm to about 20 mm. In an example, the scanning of preheat laser beam 168 and its corresponding preheat line image 170 has an associated heat diffusion length (depth) into wafer 10 in the range of from about 30 microns to about 500 microns.

With reference again to FIG. 3 and FIG. 4A, system 100 also includes a second light beam-source system 250 that generates a second light beam 268. In an example, second light beam 268 is a second laser beam of intensity $I_2$ and is used to add heat to the preheated portion of wafer surface 12 as caused by irradiation with preheat laser beam 168 (and optionally heated chuck 130) so that wafer surface temperature $T_S$ locally rises and spikes at anneal temperature $T_A$, which in an example is just below a wafer melt temperature $T_{MELT}$. The second light beam 268 is also referred to below as the anneal laser beam 268.

Figure 5D:
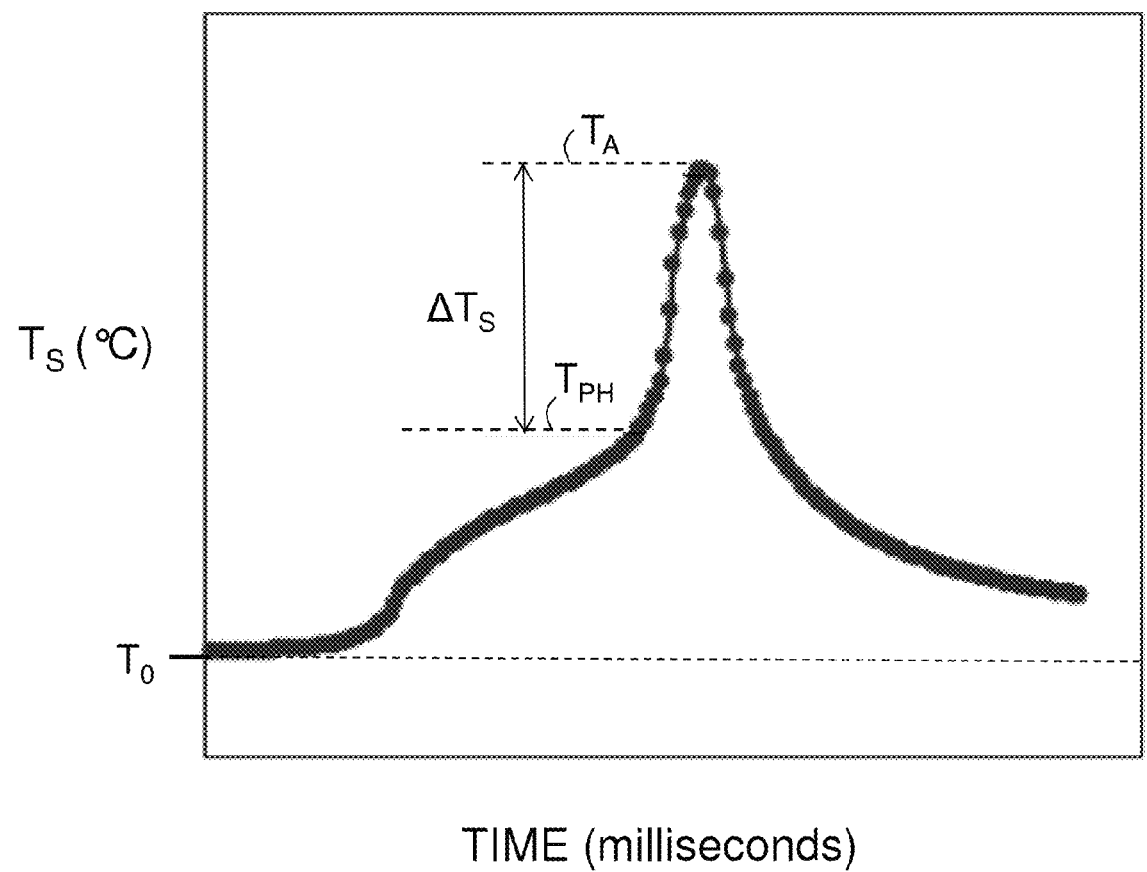
FIG. 5D plots the wafer surface temperature $T_S$ (° C.) vs. time (milliseconds) and shows a typical wafer surface temperature profile generated by the preheat and anneal laser beams.

FIG. 5D plots the wafer surface temperature $T_S$ (° C.) vs. time (milliseconds) for a given position on wafer surface 12, and shows a typical wafer surface temperature profile generated by preheat laser beam 168 and anneal laser beam 268 preheat as the beams pass over the position. The temperature $T_o$ is the base wafer surface temperature prior to the application of preheat laser beam 168 or anneal laser beam 268 to wafer surface 12. $T_{PH}$ is the preheat wafer surface temperature produced by preheat laser beam 168, and $\Delta T_S$ is the surface temperature increase from preheat wafer temperature $T_{PH}$ to the anneal temperature $T_A$ produced by anneal laser beam 268. The data in the plot of FIG. 5D is based on preheat laser beam 168 being wider in the scanning direction than anneal laser beam 268. This serves to preheat the wafer to an intermediate (preheat) temperature $T_{PH}$ before the anneal laser beam further heats the wafer surface to anneal temperature $T_A$.

In another example, second light beam 268 is a narrow-band light beam centered at processing a (second) wavelength $\lambda_2$ of the second light beam, and is used to measure a second reflectivity $R_2(x,y)$ of wafer surface 12 at the second wavelength $\lambda_2$, as described below. As the discussion below is initially directed to laser annealing, second light beam-source system 250 is hereafter referred to as anneal laser system 250 and the at least one second light beam 268 is referred to as anneal laser beam 268 unless otherwise noted.

In an example, anneal laser system 250 includes an anneal laser 260 that generates an initial anneal laser beam 262. The second wavelength $\lambda_2$ of second light beam 268 is referred to as the anneal wavelength, and can be any wavelength that can heat wafer surface 12 after it has been preheated. Example anneal wavelengths include IR, visible or ultraviolet (UV) wavelengths.

The anneal laser system 250 also includes an anneal optical system 266 operably arranged relative to anneal laser 260 along a second (anneal) optical axis A2. An example anneal optical system 266 includes a beam-shaping optical system 266A, a fold-mirror FM1, an adjustable aperture 267, a projection optical system 266B and optionally another fold mirror FM2. The anneal optical system 266 is configured to receive initial anneal laser beam 262 from anneal laser 260 and to form therefrom anneal laser beam 268. The anneal laser beam 268 forms at wafer surface 12 a second (anneal) line image 270 relative to preheat line image 170 so that that the aforementioned annealing occurs. In an example embodiment, second (anneal) optical axis A2 has an incident angle $\theta_2$ to wafer surface 12 at or near the Brewster angle for silicon, though any reasonable incident angle for second optical axis A2 can be employed.

In an example, the intensity $I_2$ of anneal laser beam 268 is selected to raise the temperature of wafer surface 12 by between 200° C. and 800° C., depending on the preheat temperature $T_{PH}$. In an example, the intensity $I_2$ raises the wafer surface temperature from the preheat wafer surface temperature $T_{PH}$ up to the anneal temperature $T_A$, which in an example is just below the melting temperature of silicon.

FIG. 5A also includes a plan schematic view of an example idealized anneal line image 270 as formed on wafer surface 12 relative to preheat line image 170. FIG. 5B and FIG. 5C also include X-direction and Y-direction cross-sectional plots of an example intensity profile 270P for anneal laser beam 268. Intensity profile 270P defines anneal line image 270, e.g., by virtue of the intensity being above a threshold intensity $I_{TH}$. The anneal line image 270 has a length L2 in the Y-direction and a width W2 in the X-direction.

Figure 5E:
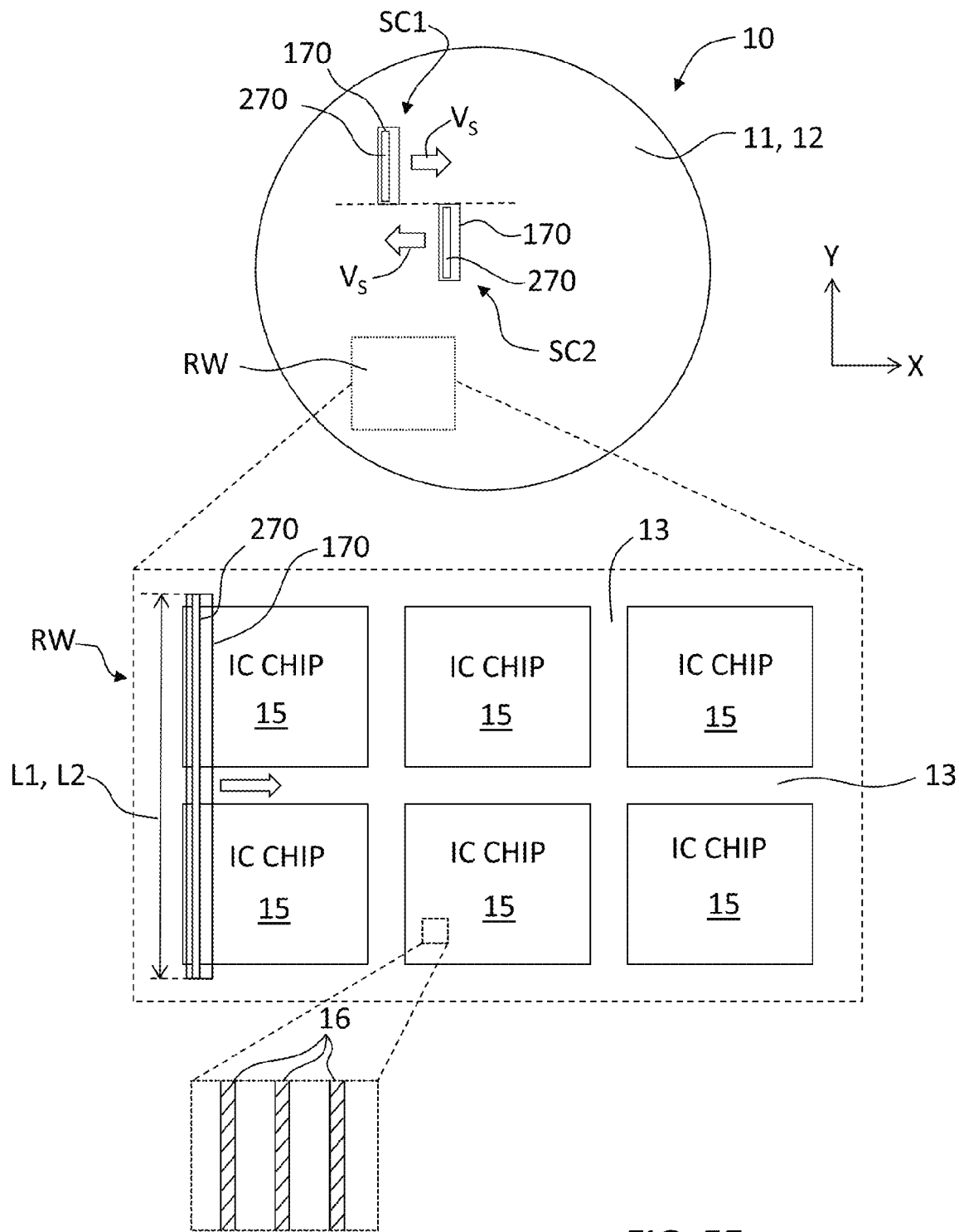
FIG. 5E is a plan view of an example wafer that includes a close-up inset illustrating an example region RW of the wafer surface that includes IC chips, and also a second close-up inset illustrating an example wafer feature within the IC chip.

FIG. 5E is a plan view of an example wafer 10 that includes a close-up inset illustrating an example region RW of wafer surface 12. The region RW includes a number of IC chips 15 spaced apart by gaps 13, e.g., a kerf region or a region used to form scribe lines for dicing the IC chips. Example wafer features 16 are also shown within IC chips 15. The example wafer features 16 are shown by way of example as metallization lines within IC chip 15, the metallization lines being oriented in the Y-direction.

The intensity profile 270P as taken along the scanning direction typically has a Gaussian form. In an example, the width W2 of anneal line image 270 is defined by the FWHM of a Gaussian Y-directional cross-section of intensity profile 270P. A typical width W2 is in the range of 50 microns to 500 microns. In an example, the length L2 of anneal line image 270 is substantially the same as the length L1 of preheat line image 170.

With reference again to FIG. 3 and FIG. 4A, system 100 includes a first photodetector 280 arranged relative to wafer surface 12 to detect a specularly reflected laser beam 168R that reflects from the wafer surface. The first photodetector 280 generates an electrical signal SD1 representative of the intensity of the detected reflected laser beam 168R. In an example photodetector 280 includes a cooled (e.g., thermal-electric cooled or liquid-nitrogen cooled) infrared detector.

System 100 also includes a second photodetector 290 arranged to detect reflected or scattered laser light 268RS from wafer surface 12. In an example, photodetector 290 includes an integrating sphere 292 and a photodiode 294 that is operably attached thereto and in optical communication with the interior of the integrating sphere. The photodetector 290 generates an electrical signal SD2 representative of the intensity of the detected reflected and scattered laser light 268RS. Note that if a short wavelength anneal laser 260 is used to generate anneal laser beam 268, the amount of scattering of the anneal laser beam from patterned wafer surface 12 may be significant. Hence, in an example, integrating sphere 292 is employed to collect both the specular reflected and scattered light 268RS.

The system 100 further includes a system controller 300 electrically connected to stage controller 124, chuck controller 134, preheat laser 160, anneal laser 260, adjustable aperture 267, and first and second photodetectors 280 and 290. In an example, system controller 300 comprises a computer or like machine that is adapted (e.g., via instructions such as software embodied in a computer-readable or machine-readable medium) to cause the controller to control the operation of the various components of system 100. The system controller 300 includes a processor unit ("processor") 302 and a memory unit ("memory") 304. An example controller 300 is or includes a computer with a processor and includes an operating system such as Microsoft WINDOWS or LINUX.

In an example embodiment, processor 302 is or includes any processor or device capable of executing a series of software instructions and includes, without limitation, a general- or special-purpose microprocessor, finite state machine, controller, computer, central-processing unit (CPU), field-programmable gate array (FPGA) or digital signal processor. In an example embodiment, the processor is an Intel XEON or PENTIUM processor, or an AMD TURION or other in the line of such processors made by AMD Corp., Intel Corp. or another semiconductor processor manufacturer.

The memory 304 is operably connected to processor 302. As used herein, the term "memory" refers to any processor-readable medium, including but not limited to RAM, ROM, EPROM, PROM, EEPROM, disk, floppy disk, hard disk, CD-ROM, DVD or the like, on which may be stored a series of instructions executable by processor 302. In an example embodiment, controller 300 includes a disk drive 306 adapted to accommodate a removable processor-readable medium 308, such as CD-ROM, DVE, memory stick or like storage medium.

The laser annealing methods described herein may be implemented in various embodiments in a machine-readable medium (e.g., memory 304) comprising machine readable instructions (e.g., computer programs and/or software modules) for causing controller 300 to perform the annealing methods described herein by controlling the operation of system 100. In an example embodiment, the computer programs run on processor 302 out of memory 304.

The computer programs and/or software modules may comprise multiple modules or objects in order to perform the various methods of the present disclosure and to control the operation and function of the various components in system 100 and in reflectivity measurement system 100RM. The type of computer programming languages used for the code may range from procedural code-type languages to object-oriented languages. The files or objects need not have a one-to-one correspondence to the modules or method steps described. Further, the method and system may comprise combinations of software, hardware and firmware. Firmware can be downloaded into processor 302 for implementing the various example embodiments disclosed herein.

Improved Surface Temperature Uniformity

A benefit of using the two-beam laser annealing systems and methods disclosed herein is improved temperature uniformity of wafer surface 12, which is achieved by mitigating the aforementioned adverse pattern density effects that among other things create a varying reflectivity over the wafer surface. As discussed above, for certain devices such as memory chips, wafer surface 12 may comprise materials and features 16 involving high reflectivity at the long wavelengths associated with preheat laser beam 168 and lower reflectivity at the short wavelengths associated with anneal laser beam 268. Consequently, preheat laser beam 168 and anneal laser beam and 268 can be employed to reduce the optical absorption contrast, and hence provide a more uniform temperature distribution during the annealing process.

Embodiments of the methods of annealing disclosed herein include selecting intensities $I_1$ and $I_2$ of preheat laser beam 168 and anneal laser beam 268, respectively, based on the reflectivity properties of at least a portion of wafer surface 12, to achieve improved uniformity in the annealing temperature over wafer 10. In an example, the selection of intensities $I_1$ and $I_2$ is done in a manner that maximally reduces temperature variations in wafer surface 12 during the annealing process.

In an example, the ratio $RI=I_1/I_2$ is used as a parameter for optimizing the annealing process to achieve a reduced or minimized temperature variation in wafer surface 12 during the annealing process. In an example, intensities $I_1$ and $I_2$ are varied during scanning based on first and second reflectivity maps for at least a portion of wafer surface 12. In an example, the variation is carried out over a scale that is at least the size of an anneal line image 268P, since the intensity of the anneal line image does not vary over its length. Generally, the frequency of any change in intensity $I_1$ and/or $I_2$ varies slowly relative to the spatial frequency of the wafer surface reflectivity at preheat and anneal wavelengths $\lambda_1$ and $\lambda_2$.

Figure 8B:
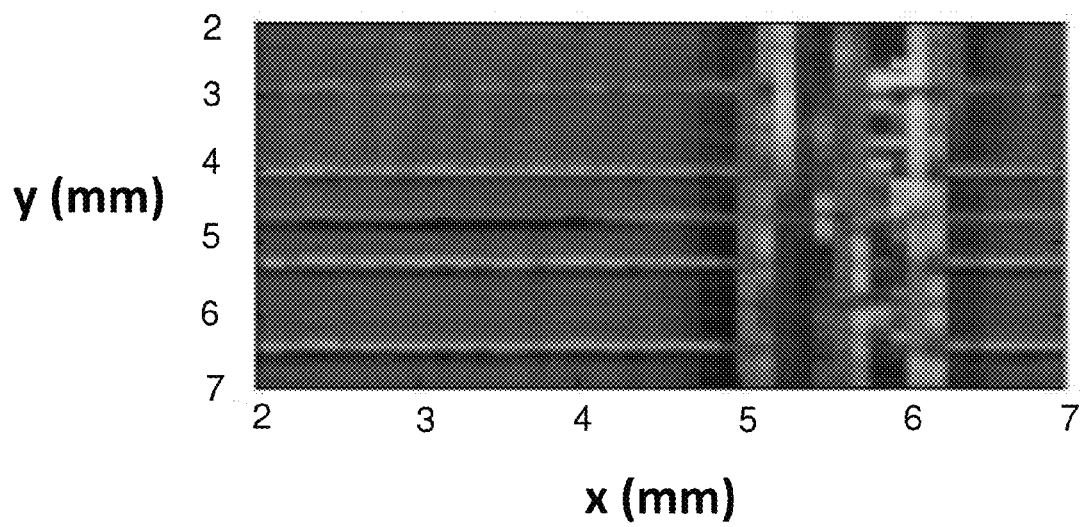
FIG. 8A and FIG. 8B are similar to FIG. 6A and FIG. 7A and show a two-dimensional (x,y) reflectivity map and a reflectivity vs. position plot (i.e., a one-dimensional reflectivity map) taken at a central line based on a combination of an IR preheat wavelength of 10.6 microns and an anneal wavelength of 0.85 microns (850 nm)
Figure 8A:
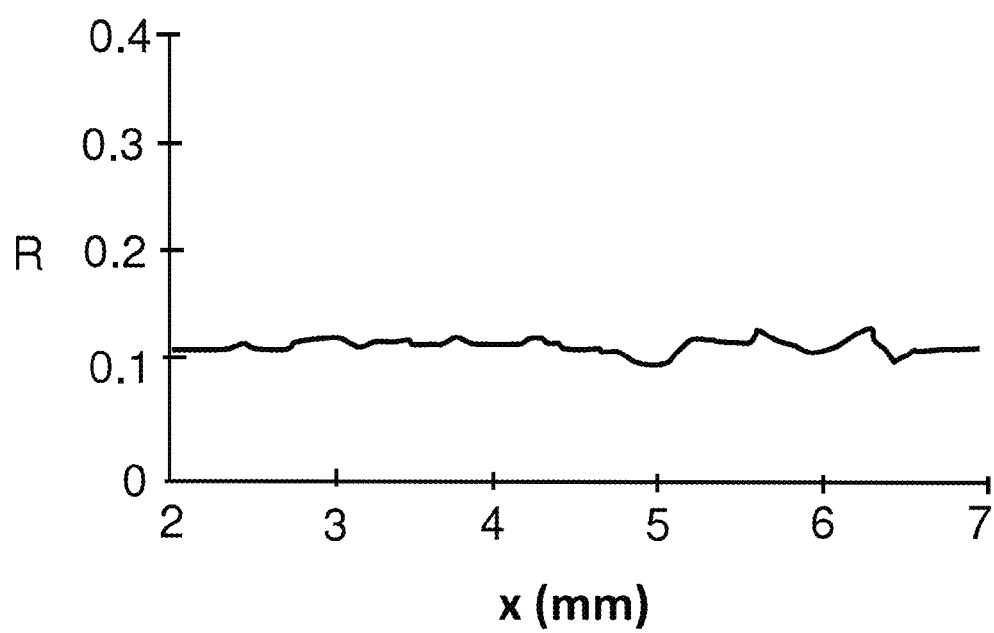

In another example, intensities $I_1$ and $I_2$ are kept constant and represent a best-choice of intensities for the particular reflectivity maps in terms of reducing or minimizing the variation in the wafer surface temperature during the annealing process. An example of this best-choice method is illustrated in FIG. 8A and FIG. 8B as discussed below.

The reflectivity of at least a portion of wafer surface 12 can be measured using system 100 as described above using preheat laser beam 168 and anneal laser beam 268. More generally, the reflectivity of at least a portion of wafer surface 12 can be measured using reflectivity measurement system 100RM (or a similarly configured system) that utilizes first and second light beam 168 and 268 as either laser or non-laser (e.g., lamp-generated) beams that have the same wavelengths as preheat and anneal wavelengths $\lambda_1$ and $\lambda_2$, which are used to anneal wafer 10. The discussion below is directed to the measurement of the reflectivity of wafer surface 12 using preheat and anneal laser beams 168 and 268 by way of example. The typical laser power used for establishing the first and second reflectivity maps over at least a portion of wafer surface 12 at preheat and anneal wavelengths $\lambda_1$ and $\lambda_2$ need not be as high as the annealing power, and can be in the milliwatt range.

Figure 4B:
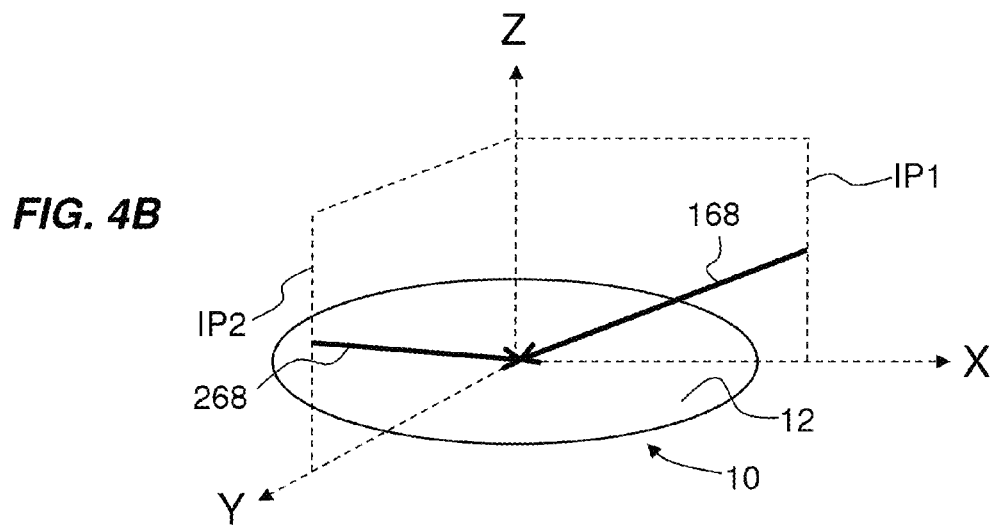
FIG. 4B is a schematic diagram based on FIG. 4A and shows the first and second incident planes for the preheat and anneal laser beams as defined by the X-Z plane and the Y-Z plane, respectively.

With reference to FIG. 4B, in an example, preheat laser beam 168 and anneal laser beam 268 reside in respective first and second incident planes IP1 and IP2 that are perpendicular to each other. In particular, first incident plane IP1 is defined by the X-Z plane and second incident plane IP2 is defined by the Y-Z plane. The reflected first light beam 168R is detected by first photodetector 280 along a specular reflection path. The reflected and scattered second light beam 268RS is collected by second photodetector 290. The controller 300 controls wafer stage 120 to effectuate X-Y scanning in a defined area of wafer surface 12 that in an example covers an integer number of IC chips 15. The detector signals SD1 and SD2 from respective photodetectors 280 and 290 are generated as a function of the (x,y) wafer coordinates and are provided to controller 300. By knowing the respective intensities $I_1$ and $I_2$ of first light beam 168 and second light beam 268, and by measuring the respective reflected intensities $I_1'$ and $I_2'$ of reflected first light beam 168R and reflected and scattered second light beam 268RS, the reflectivity at a given x-y location on wafer surface 12 can be determined, e.g., by processor 302.

Thus, reflectivity data is collected from wafer surface 12 as a function of x-y coordinates to create reflectivity maps $R_1(x,y)$ and $R_2(x,y)$ of at least a portion of the wafer surface. In an example, a calibrated wafer having a high reflectivity for the wavelengths associated with first and second light beams 168 and 268, such as a metal-coated silicon wafer, is used to calibrate the reflectivity measurements. As discussed above, the reflectivity mapping of wafer surface 12 can be carried out in an actual LSA annealing system or in a separate metrology system such as system 100RM.

FIG. 6A and FIG. 6B are contour plots of reflectivity that represent reflectivity maps of an example wafer surface 12 as measured at preheat wavelength $\lambda_1$ (FIG. 6A) and anneal wavelength $\lambda_2$ (FIG. 6B). FIG. 7A and FIG. 7B are reflectivity plots as a function of position for the contour plots of FIG. 6A and FIG. 6B taken along the lines A-A'. The lower reflectivity region at preheat wavelength $\lambda_1$ shows a higher reflectivity at anneal wavelength $\lambda_2$, indicating that the combination of the two wavelengths can partially compensate for the variation in the reflectivity of wafer surface 12.

FIG. 8A and FIG. 8B are similar to FIG. 6A and FIG. 7A and show the reflectivity map and cutline for when first and second light beams 168 and 268 are used. The ratio RI of the two laser beam intensities $I_1$ and $I_2$ is chosen to give the most uniform absorption. For this application, it is desirable that the first and second light beams 168 and 268 have a similar size at wafer surface 12 so that the annealing time from each laser does not differ significantly.

In an example embodiment, the optimal intensity ratio $RI=I_1/I_2$ is determined by minimizing the within-chip temperature distribution during annealing. This can be estimated based on the following equation for the wafer surface temperature:

$$T_S(x,y)=s_1 \cdot A_1(x,y) \cdot I_1 + s_2 \cdot A_2(x,y) \cdot I_2$$

The variables $s_1$ and $s_2$ are coefficients that represent the sensitivity of the wafer temperature to the absorbed intensity. These coefficients can be determined by annealing un-patterned silicon wafers and monitoring the temperature as a function of absorbed laser intensity.

The parameters $A_1$ and $A_2$ are the absorption distributions as calculated from the measured reflectivity maps $R_1$ and $R_2$ via the relationships:

$$A_1(x,y) = 1 - R_1(x,y)$$

$$A_2(x,y) = 1 - R_2(x,y),$$

where $R_1$ and $R_2$ are the reflectivity maps as measured according to the methods described above. When integrating sphere 292 is used, the measured reflectivity map also includes the scattering contributions.

In the above example, second light beam 268, which has a different wavelength than first light beam 168, was used to generate an absorption distribution that partially compensates for the absorption variation associated with the first light beam. Since optical absorption also varies with the angle of incidence, polarization and orientation of the incident plane with respect to features 16 on wafer surface 12 (e.g., the IC chip circuit layout), second light beam 268 with either a) the same wavelength and at least one or more of a different angle of incidence, polarization and incident plane orientation or b) a different wavelength and either the same or different orientation, can be employed to improve absorption uniformity and thus anneal temperature uniformity.

By way of example, consider the case where wafer surface 12 has IC chips 15 whose layout has features 16 with metal grating lines running in both x and y directions. The features 16 that have grating lines parallel to the light incident plane (assuming p-polarization) will have a higher reflectivity than those perpendicular to the incident plane. In this case, second light beam 268 can have the same wavelength, angle of incidence and polarization as first light beam 168, but with an incident plane that is orthogonal to that of the first light beam.

Figure 9:
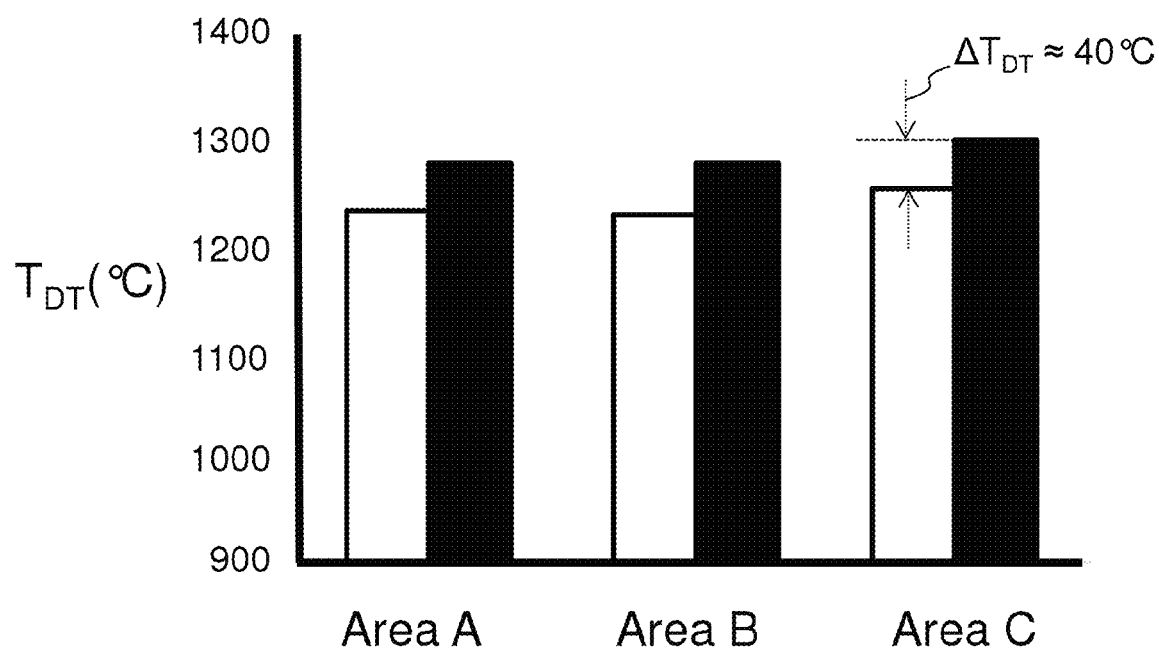
FIG. 9 is a bar chart that compares the edge damage threshold temperatures $T_{DT}$ (° C.) observed in three different layout areas of a test wafer using conventional single-beam annealing (white bars) and using the two-beam annealing systems and methods disclosed herein (black bars)

The respective intensities $I_1$ and $I_2$ of first and second light beams 168 and 268 can also be optimized to reduce the edge temperature overshoot and therefore improve the edge damage threshold. FIG. 9 is a bar chart that compares the edge damage threshold temperatures $T_{DT}$ (in ° C.) observed in three different layout areas A, B and C of a test wafer using conventional single-beam annealing (white bars) and using the two-beam annealing systems and methods disclosed herein (black bars). The two-beam annealing systems and methods provide about a 40° C. improvement in damage threshold temperature $T_{DT}$ over the prior art single-beam annealing method (i.e., $\Delta T_{DT} \approx 40°$ C. as shown in the chart).

Figure 10:
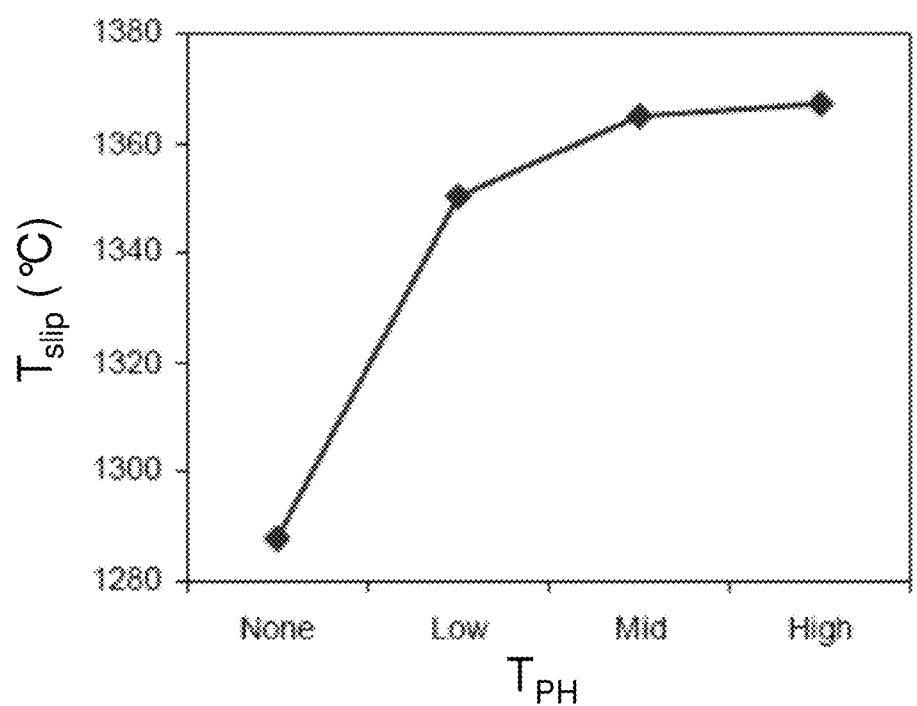
FIG. 10 is a plot of the slip threshold temperature as measured using conventional annealing and the two-beam laser annealing systems and methods disclosed herein.

An added benefit of using the two-beam annealing systems and methods disclosed herein to preheat wafer surface 12 is a reduced temperature ramping rate and reduced thermal gradient, which can be used to reduce slip generation in silicon substrate 10. FIG. 10 is a plot of the slip threshold temperature $T_{slip}$ (° C.) vs. the relative temperature $T_{PH}$ of the preheat laser beam 168, including the case "none" where no preheat laser beam was employed. The laser annealing experiments were performed on bare silicon wafers implanted with boron (implant dose: $2 \times 10^{15}$ cm$^{-2}$; energy: 5 keV). The slip thresholds were determined by optical microscope inspection. A significant improvement in slip threshold temperature $T_{slip}$ is observed relative to the "none" case (i.e., prior-art single-beam annealing) for increasing preheat temperature $T_{PH}$.

Annealing Methods

Once the first and second wafer surface reflectivity maps $R_1(x,y)$ and $R_2(x,y)$ of wafer 10 are established as described above, the methods disclosed herein include annealing the wafer using system 100 by selecting preheat and anneal laser beam intensities $I_1$ and $I_2$ based on the first and second reflectivity maps so that temperature non-uniformities of the annealing process are reduced as compared to prior art single-beam annealing.

Thus, with reference again to FIG. 3 and system 100 therein, in an example system controller 300 sends a first control signal S1 to preheat laser 160, which in response thereto generates initial preheat laser beam 162. This initial preheat laser beam 162 is received by preheat optical system 166, which forms therefrom preheat laser beam 168 of intensity $I_1$. The preheat laser beam 168 travels generally along first optical axis A1 and forms preheat line image 170 at wafer surface 12.

The system controller 300 also sends a second control signal S2 to anneal laser 260, which in response thereto generates initial anneal laser beam 262. This initial anneal laser beam 262 is received by anneal optical system 266, which forms therefrom anneal laser beam 268 having intensity $I_2$. The anneal laser beam 268 forms an anneal line image 270 relative to preheat line image 170 so that the aforementioned local wafer surface annealing occurs.

The system controller 300 also sends a third control signal S3 to stage controller 124 to move (scan) wafer 10 relative to preheat and anneal line images 170 and 270. In an example where chuck 130 provides wafer preheating, system controller 300 may also send a fourth control signal S4 to chuck controller 134 to initiate the wafer preheating process. The system controller 300 optionally sends a fifth control signal S5 to adjustable aperture 267 to optionally set the length L2 and width W2 of anneal line image 270. As discussed above, in one example, preheat and anneal intensities $I_1$ and $I_2$ remain constant as wafer surface 12 is annealed. In another example, at least one of preheat intensity $I_1$ and anneal intensity $I_2$ is varied during the scanning of the preheat and anneal laser beams 168 and 268 based on first and second reflectivity maps $R_1(x,y)$ and $R_2(x,y)$ as stored in controller 300. In an example, the modulation of at least one of preheat intensity $I_1$ and anneal intensity $I_2$ is based on an average of the reflectivity measurements in each of the reflectivity maps $R_1(x,y)$ and $R_2(x,y)$.

The dwell time $t_D$ of preheat line image 170 is given by the ratio of line-image width W1 to scanning velocity $V_S$. In an example, dwell time $t_D$ is in the range of 100 microseconds ($\mu$s) $\leq t_D \leq$ 20 millisecond (ms).

In the above discussion, first laser beam 168 has a long wavelength, is oriented substantially at the Brewster angle of incidence and is used as a preheat beam while the second laser beam has a shorter wavelength, or a similar wavelength but different configuration, and is used as the anneal laser beam. Other embodiments of the disclosure include using the long-wavelength laser beam as the anneal laser beam and the short-wavelength laser beam as the preheat beam.

It will be apparent to those skilled in the art that various modifications and variations can be made to the present disclosure without departing from the spirit and scope of the disclosure. Thus it is intended that the present disclosure cover the modifications and variations of this disclosure provided they come within the scope of the appended claims and their equivalents.

What is claimed is:

1. A method of non-melt annealing a semiconductor substrate having a patterned surface and a melt temperature, comprising:
   scanning at least one first laser beam over the patterned surface, the at least one first laser beam being configured in a first incidence plane and having a first wavelength and a first intensity that heats the patterned surface to a preheat temperature that is below the melt temperature and less than an anneal temperature; and scanning at least one second laser beam over the patterned surface and relative to the first laser beam, the at least one second laser beam being configured in a second incidence plane and having a second wavelength and a second intensity that heats the patterned surface from the preheat temperature up to the anneal temperature; and selecting the first and second intensities to achieve the anneal temperature while minimizing at least one of edge damage and slip generation.

2. The method of non-melt annealing according to claim 1, wherein the first wavelength is infrared and the second wavelength is different from the first wavelength.

3. The method of non-melt annealing according to claim 1, further comprising:

the first laser beam defining a preheat line image at the patterned surface;

the second laser beam defining an anneal line image at the patterned surface; and wherein the anneal line image falls entirely within the preheat line image.

4. The method of non-melt annealing according to claim 3, further comprising providing one of the preheat line image and the at least one anneal line image to have a length that corresponds to a size of a region of the patterned surface.

5. The method of non-melt annealing according to claim 1, further comprising varying at least one of the first and second intensities of the first and second laser beams during the scanning of the first and second laser beams.

6. The method of non-melt annealing according to claim 1, wherein the second laser beam increases the patterned surface temperature to the anneal temperature, wherein the amount of patterned surface temperature increase is in the range of between 200° C. and 800° C.

7. The method of non-melt annealing according to claim 6, wherein the anneal temperature is about 1,300° C.

8. The method of non-melt annealing according to claim 1, wherein the first laser beam raises the patterned surface temperature to be in the range from about 500° C. to about 1,100° C.

9. A system for laser annealing a semiconductor wafer having a patterned surface with first and second reflectivity maps at respective first and second wavelengths and an anneal temperature that is below a melt temperature of the wafer, comprising:

a first laser system configured to generate a first laser beam having the first wavelength and a first intensity and scan the first laser beam over the patterned surface in a first incident plane to heat the patterned surface to a preheat temperature;

a second laser system configured to generate a second laser beam having the second wavelength and a second intensity and scan the second laser beam over the patterned surface in a second incident plane relative to the first incident plane of the first laser beam, the second laser beam being configured to heat the patterned surface from the preheat temperature to the anneal temperature; and wherein the first and second intensities are selected based on the first and second reflectivity maps to reduce an amount of surface temperature variation during the scanning of the first and second laser beams as compared to annealing the patterned surface of the semiconductor wafer with only the second laser beam.

10. The system for laser annealing a semiconductor wafer according to claim 9, further comprising:

the first laser beam defining a preheat line image at the patterned surface;

the second laser beam defining an anneal line image at the patterned surface; and the first and second laser systems being configured so that the anneal line image resides entirely within the preheat line image.

11. The system for laser annealing a semiconductor wafer according to claim 9, further comprising a controller operably arranged to vary at least one of the first and second intensities when the first and second laser beams are scanned.

12. The system for laser annealing a semiconductor wafer according to claim 9, wherein the first wavelength is an infrared wavelength and the second wavelength is different from the first wavelength.

13. The system for laser annealing a semiconductor wafer according to claim 9, further comprising the second intensity being sufficient to increase the patterned surface temperature up to the anneal temperature, wherein the amount of patterned surface temperature increase is in the range of between 200° C. and 800° C.

14. The system for laser annealing a semiconductor wafer according to claim 13, wherein the second laser beam defines the anneal temperature to be about 1,300° C.

15. The system for laser annealing a semiconductor wafer according to claim 9, wherein the first laser beam defines the pre-heat temperature to be in the range from about 500° C. to about 1,100° C.

16. The system for laser annealing a semiconductor wafer according to claim 9, further comprising:

the first laser beam defining a preheat line image at the patterned surface, the pre-heat line image has a length L1 in the range 5 mm≤L1≤20 mm.

17. The system for laser annealing a semiconductor wafer according to claim 16, further comprising:

the second laser beam defining an anneal line image at the patterned surface, the anneal line imaging having a length L2 that is substantially the same as length L1 of the pre-heat line image.

* * * * *